United States Patent [19]

Nelson

[11] Patent Number: 4,799,492

[45] Date of Patent: Jan. 24, 1989

[54] METHOD AND APPARATUS FOR INDIRECT BLOOD PRESSURE MEASUREMENT

[75] Inventor: Craig H. Nelson, Hillsboro, Oreg.

[73] Assignee: SpaceLabs, Inc., Bothell, Wash.

[21] Appl. No.: 875,440

[22] Filed: Jun. 17, 1986

[51] Int. Cl.4 .............................................. A61B 5/02
[52] U.S. Cl. .................... 128/672; 128/677; 128/900
[58] Field of Search ............ 128/677, 679, 680, 681, 128/682, 683, 900, 672

[56] References Cited

U.S. PATENT DOCUMENTS

| | | | |
|---|---|---|---|
| 4,190,886 | 2/1980 | Sherman | 128/900 |
| 4,360,029 | 11/1982 | Ramsey, III | 128/682 |
| 4,461,266 | 6/1984 | Hood, Jr. et al. | 128/677 |
| 4,484,584 | 11/1984 | Vemura | 128/680 |
| 4,501,280 | 2/1985 | Hood, Jr. | 128/677 |
| 4,638,810 | 1/1987 | Ramsey, III et al. | 128/682 |

Primary Examiner—Edward M. Coven
Assistant Examiner—John P. Lacyk
Attorney, Agent, or Firm—Seed and Berry

[57] ABSTRACT

A method and apparatus for the indirect measurement of blood pressure is disclosed. Pressure is applied to a cuff attached to a patient adjacent a blood vessel and a quantity representative of the patient's blood pressure is measured as the applied pressure is changed. A table of values of the quantity as the applied pressure is changed is formed. Valves of the table are selected as spurious high and low values in response to predetermined criteria and new values assigned to the selected values which reduces the error in calculating systolic and diastolic blood pressure from the table.

21 Claims, 4 Drawing Sheets

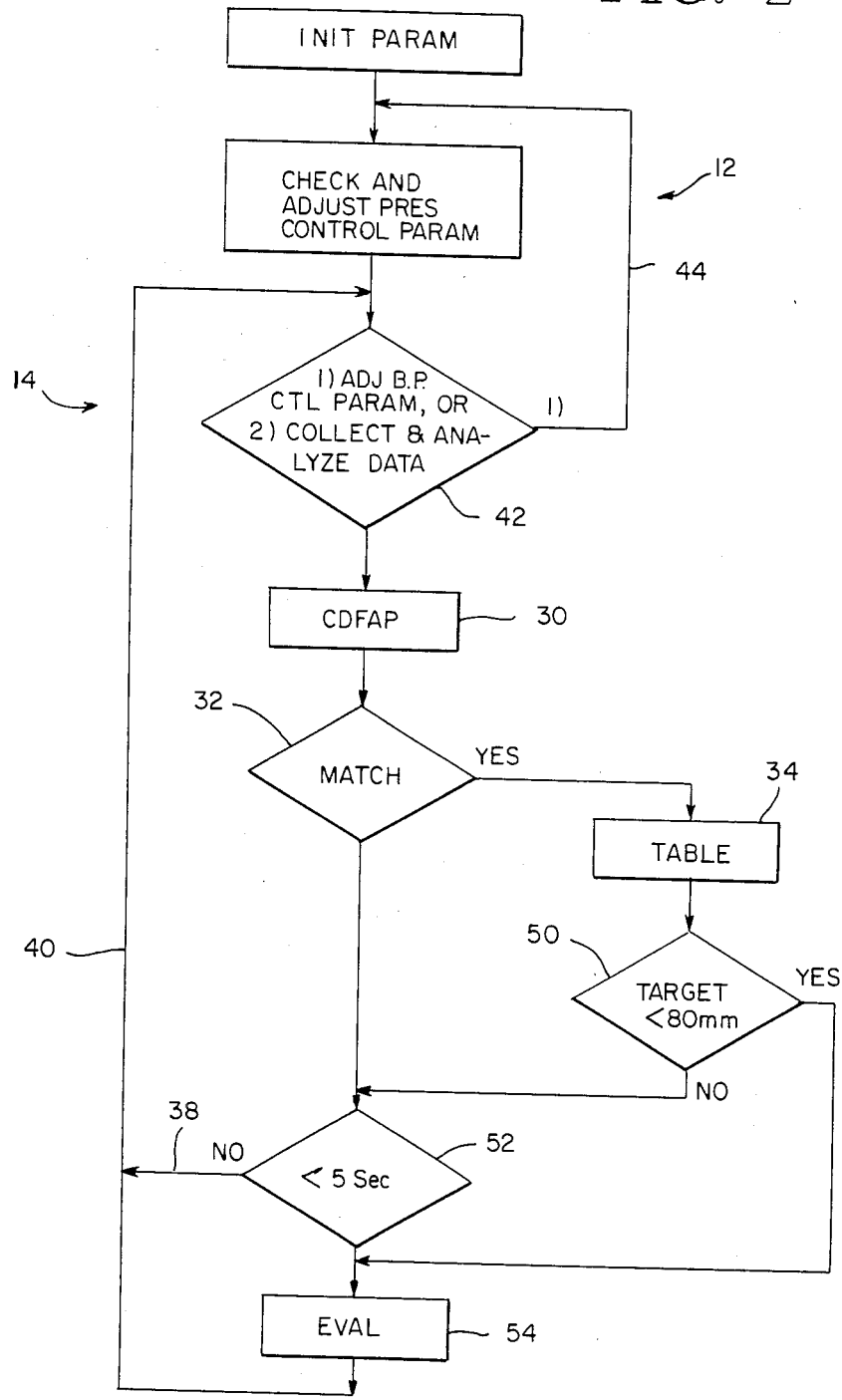

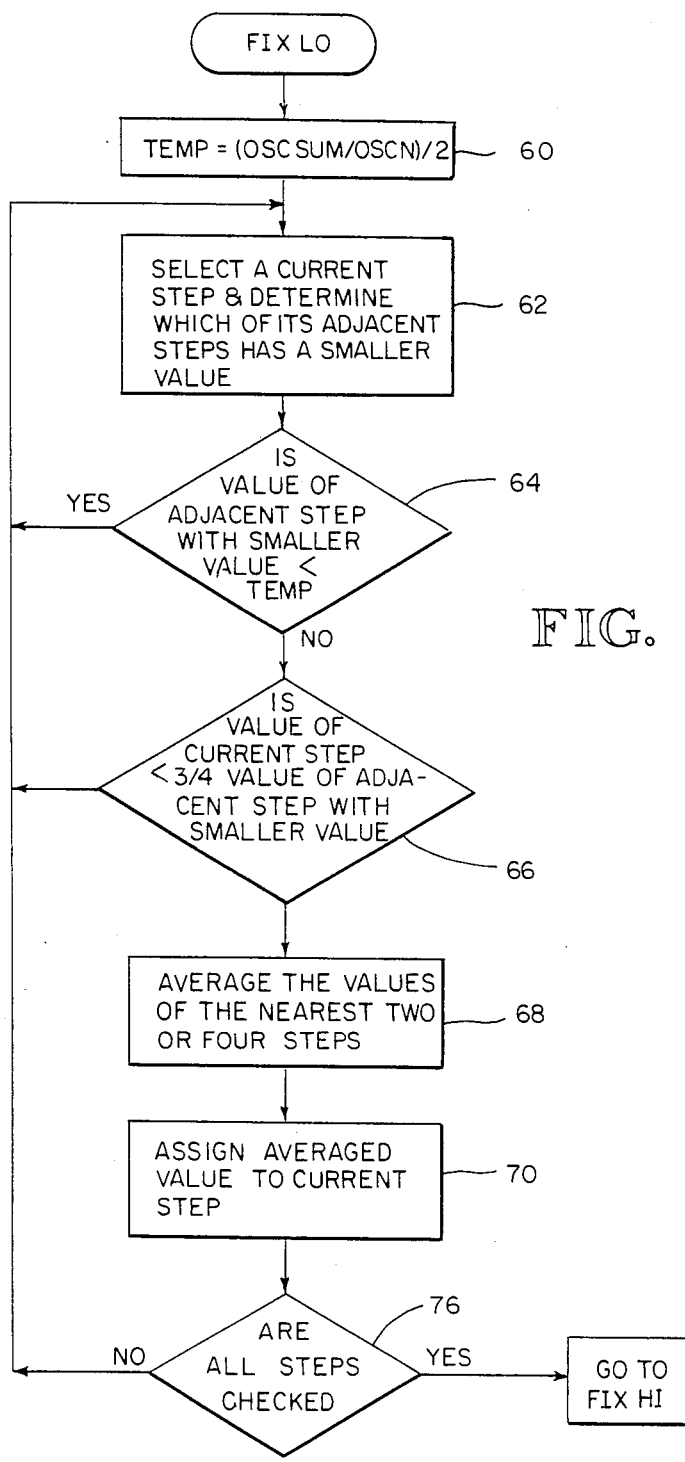

METHOD AND APPARATUS FOR INDIRECT BLOOD PRESSURE MEASUREMENT

BACKGROUND OF THE INVENTION

The present invention relates to blood pressure measurement, in particular to a method and apparatus for the indirect measurement of blood pressure.

In most automatic indirect methods of blood pressure measurement, a pressure cuff is attached to a patient's arm adjacent a blood vessel, the cuff is pressurized with an applied pressure which is high enough to occlude the blood vessel and the applied pressure is gradually reduced. As the pressure is reduced to below systolic and then diastolic, blood begins to flow through the blood vessel creating the well known Korotkoff sounds and pulsatile pressures in the blood vessel. The sounds can be detected by a microphone at pulsatile pressures by a pressure transducer. The sensor, whether a microphone or pressure transducer, measures a quantity which is representative of the patient's blood pressure.

A table is then formed of values of the quantity measured at various applied pressures as the applied pressure is gradually changed. Using the table the systolic and diastolic blood pressures are determined.

In a well behaved reading of blood pressure, the values generally increase from low values at applied pressures above the systolic to a maximum value at applied pressures between systolic and diastolic. Similarly, the values generally increase from low values at applied pressures less than diastolic to the maximum values. In some cases, however, spurious high or low values in the table can occur due to patient movement, etc., which can and often do cause erroneous determinations of systolic and diastolic blood pressures. It is desirable therefore to detect and eliminate the spurious high and low values in the table when they occur.

SUMMARY OF THE INVENTION

The present invention provides for automatically readjusting spurious low and high values in a table of values formed from the indirect measurement of blood pressure. In the preferred embodiment the oscillometric method of blood pressure measurment is used but the invention is applicable to auscultatory blood pressure measurement as well.

The present invention provides for selecting in response to predetermined criteria those values which are spurious high or low values. Then either one or two values in the table on either side of the selected value are averaged and this value is substituted for the selected value. In the case of suspected low values the smaller of the immediately adjacent values is chosen and compared with a predetermined threshold value. If it is larger than the threshold then the candidate value is compared with the smaller value and if less than 75% of the smaller, it is reassigned the average value of the four most adjacent values.

For larger values suspected to be too large, if the two largest values in the table are not adjacent and if the larger neighbor adjacent to a candidate value is less than fifty per cent of the calculated value then the candidate value is re-assigned with the average value of the two most immediate neighbors.

BRIEF DESCRIPTION OF THE DRAWINGS

FIG. 2 is a block diagram flow chart of the overall operation of the apparatus of FIG. 1.

FIG. 6 is a more detailed block diagram flow chart of a first portion of the block diagram of FIG. 2

DETAILED DESCRIPTION OF THE DRAWINGS

Figure 1:
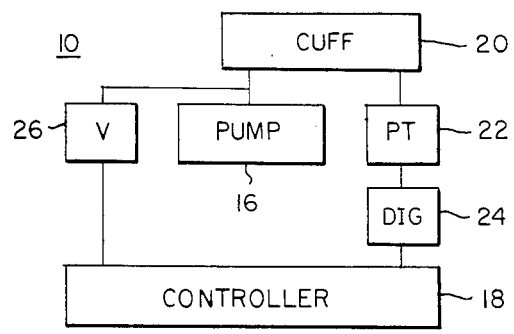
FIG. 1 is a block diagram of an apparatus for the indirect measurement of blood pressure.
Figure 3:
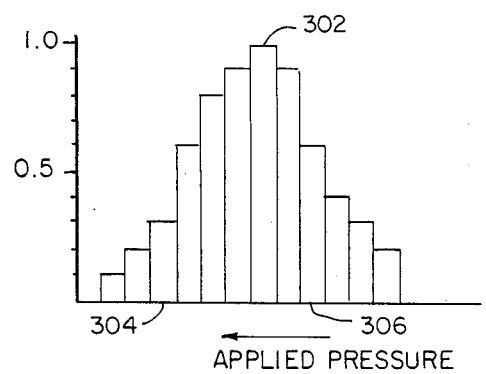
FIG. 3 is a graphic representation of a table of well behaved values formed during the operation of the blood pressure measurement of FIG. 1.

Referring now to the figures, the system designated generally 10 in FIG. 1 operates in basically two loops, a blood pressure control loop 12 (bp loop) and a collect and analyze data loop 14 (cd loop) in FIG. 2. Initially, a pump 16 under the control of a controller 18 in the bp loop 12 pumps up the pressure in a cuff 20 located on the patent's arm to a predetermined level, e.g. 165 millimeters (mm) of mercury. A pressure transducer 22 senses the applied pressure in the cuff and any variations due to pressure pulses in the arm's artery due to the beating of the heart. The electrical output signal from the transducer is sampled and digitized in digitizer 24 and the samples sent to the controller 18 for processing. The gain and dynamic range of the signals are checked and adjusted at this time as well. The cd loop 14 is exercised by the controller 18 on the digital data collected so far, and when completed the bp loop 12 again takes over and bleeds pressure from the cuff 20 through a valve 26 under the control of the controller 18. The pressure each time is bled down in predetermined increments, e.g., 4 or 6 or 8 mm. At each applied pressure level, the collect and analyze data loop 14 is exercised to obtain an oscillometric amplitude value representative of pulsatile pressure in the blood vessel occurring at that particular applied pressure step. FIG. 3 shows a typical bar graph showing the normalized values of the peaks of the oscillometric variations at each of the applied cuff pressure steps.

When in the collect and analyze data loop 14, the system first collects data for a peak of the oscillometric variations at a chosen applied pressure level 30. Samples of the variations are provided every millisecond and their amplitudes are checked until a peak amplitude is determined. This process takes about 150 milliseconds before a peak is formed. The peak is compared with the previous peak measured for the same applied blood pressure level. If a match occurs 32, the value of the peak is entered into an oscillometric value table 34. If no peak is found, zero is entered. If two peaks don't match, the search continues until a match occurs. This procedure helps to eliminate artifacts due to noise, patient movement, etc. Typically, a match is found in about two seconds. The system then returns to the blood pressure control loop via line 38, 40, decision box 42 and line 44 where the applied pressure is bled down one more step and the process to find and match a peak and enter the value into the table is repeated.

Eventually either the applied pressure will fall below a predetermined level 50 or the length of time for which the cuff has been pressurized will approach a predetermined interval 52. In either case this triggers the system to evaluate the table to see if a determination of systolic and diastolic pressures can be made from the table 54. In the preferred embodiment the predetermined applied pressure is 80 mm and the predetermined time duration of cuff pressurization is within 5 seconds of a 116 second time out criteria. If systolic and diastolic pressure calculations are unobtainable by the end of 116 seconds, the blood pressure control loop bleeds down the cuff pressure to zero.

During the evaluation phase 54, the system checks to see if there is at least three non-zero oscillometric values in the table. If there are, the highest value in the table is determined. Systolic and diastolic values are determined by looking at applied cuff pressures in the table 34 associated with oscillometric values bearing some relationship to the maximum oscillometric value in the table e.g., systolic is the applied pressure of the first step which has an oscillometric value just below fifty percent of the maximum oscillometric value on the high applied pressure side of the maximum value while diastolic is the applied pressure of the first step just below seventy-five percent of the maximum value on the low applied pressure side of the maximum.

FIG. 3 is a graphic representation of an ideal table generated as described above which has a clearly defined single maximum value 302 and clearly defined systolic and diastolic pressures 304 and 306, respectively. Sometimes, however, because of sudden patient movement or patient shivering, etc., very high oscillometric table values and very low oscillometric table values can occur in the table where they are not wanted and which can cause errors when calculating the systolic and diastolic pressures as described above. See for example in FIG. 4 the spurious low values, and in FIG. 5 the spurious high values. Means are provided within EVAL 54 for fixing these lows and highs.

Figure 4:
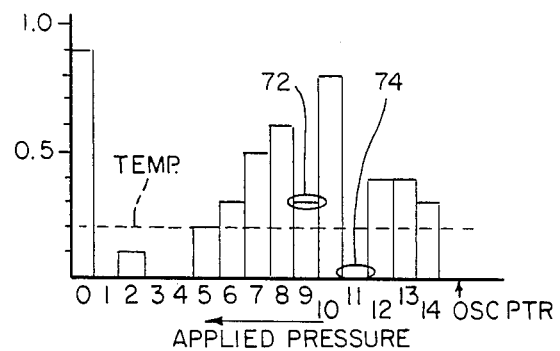
FIG. 4 is a graphic representation of a table of values formed during the operation of the apparatus of FIG. 1 containing a number of spurious low values.
Figure 5:
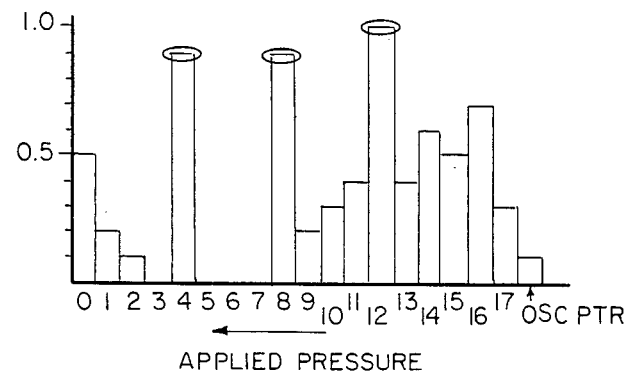
FIG. 5 is a graphic representation of a table of values formed during the operation of the apparatus of FIG. 1 containing a number of spurious high values.
Figure 7:
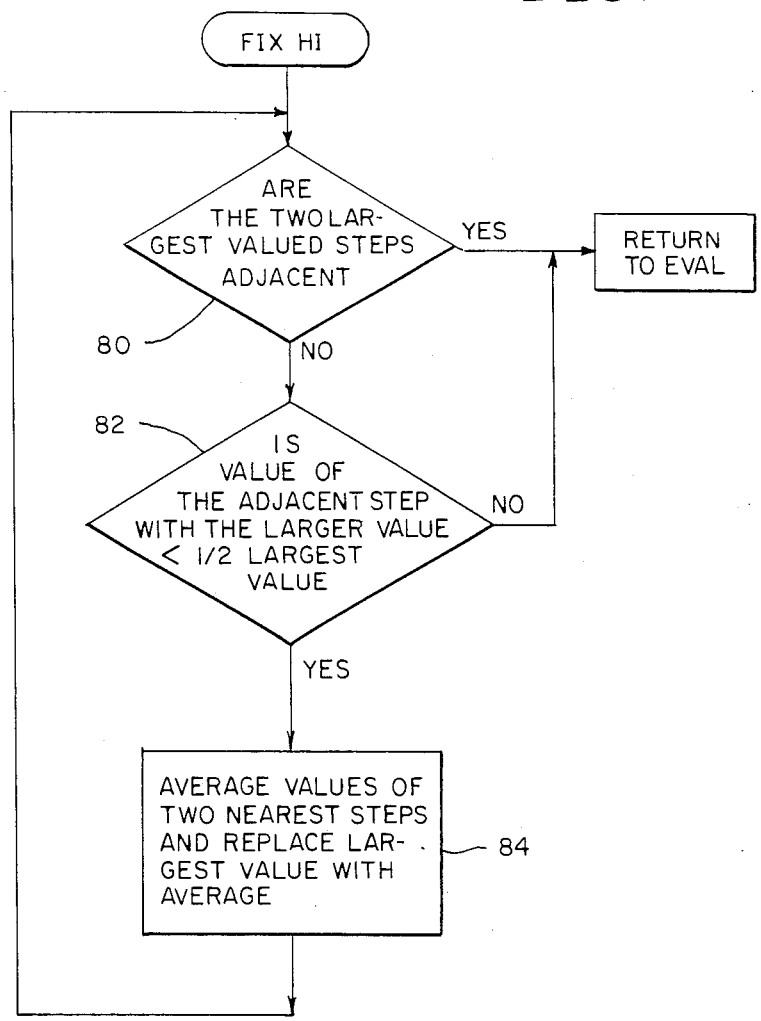
FIG. 7 is a more detailed block diagram flow chart of a second portion of the block diagram of FIG. 2.

Referring now to FIG. 6, a flow chart shows how the system fixes spurious low oscillometric values in a table such as that shown in FIG. 4. Each table has a number of applied pressure step entries ranging from step 0 at the first step at the high applied pressure end of the table to step OSCPTR, the last entry at the low applied pressure end of the table. First a TEMP value equal to ½ the average value of all the non-zero oscillometric value entries in the table is calculated 60. Ignoring the zero step and the OSCPTR step the system begins with step No. 1 and determines which of its adjacent steps has the smaller oscillometric value (e.g., step 0 or step 2) 62. (In the case of FIG. 4 it is step 2.) If the adjacent step with the smaller oscillometric value is less than the TEMP value then the current step being evaluated is not to be fixed 64. This is because most likely the low value occurs at a far end of the graph where it is likely not to be important.

If the value of the smaller valued adjacent step is larger than TEMP then the value of the current step is compared with ¾ of the value of the smaller valued step 66. If the oscillometric value of the current step is smaller than this, then a decision is made to fix the value. If the current step is the second step or second to the last step then the oscillometric values of one step on each side of the current step are averaged together and the value assigned to the current step; otherwise, the values of the two steps on each side of the current step are averaged and the average value assigned to the current step in the table. See 68 and 70. In this way spurious lows are fixed. Using this method, the low values at steps 9 and 11 would be fixed indicated by the circles 72 and 74, while the values at steps 1, 3 and 4 would be left alone. When all the steps in the table are checked for fixing the system goes on to fix the high values 76.

To fix the spurious highs in the table, the end samples 0 and OSCPTR are ignored. The steps with the two largest oscillometric values are determined and they are checked to see how close together they are 80. For example, if they are adjacent then neither is to be considered an artifact and neither will be fixed. Where applied pressure bleed steps are small; e.g. 4 mm, the criteria for determining whether an artifact exists or not could be different, e.g., if the two largest valued steps are adjacent or only separated by one step then they are not to be consiered artifacts.

If, the two steps with the largest values do not meet the above criteria then the larger valued adjacent step to the step with the largest oscillometric value is compared with one half the value of the largest valued step 82. If the value of the larger adjacent step is less than one half the largest value then the values of the steps on either side of the step with the largest value are averaged together and the average assigned to the step with the largest value 84. Following this the step with the largest peak is again found and the process is repeated.

Using the above FIX HI method, the steps 4, 8 and 12 in FIG. 6 would be fixed while steps 0, 14 and 16 would be left alone.

After the FIX LO and FIX HI routines are complete the adjusted table values are used for the determination of systolic and diastolic pressures within EVAL. If no systolic has been determined, the blood pressure control loop pumps up the pressure in the cuff (after a patient safety period has expired) to an applied pressure larger than before since it is assumed that the previous highest applied pressure wasn't high enough to measure systolic as described earlier. If the pressure bleeds below 80 mm 50 or there is less than five seconds of measurement before time out 52 then the collect data and analyze loop and EVAL routine are repeated until a diastolic pressure is determined or until the applied pressure drops 20 mm.

In the preferred embodiment the FIX LO routine is performed before the FIX HI routine, otherwise normal values might be treated as spurious high values if the normal values are adjacent spurious low values. When spurious low values are fixed first, the TEMP criteria 64 prevents the system from elevating normal low values next to a spurious high value.

It should be appreciated that even though the above method for fixing highs and lows in a sample table has been described in the context of the oscillometric method of indirect blood pressure measurement, the same method is applicable to the auscultatory methods where a microphone produces the electrical output signals instead of a pressure transducer.

I claim:

1. In an apparatus for the measurement of blood pressure in which a table of values is generated indicative of blood pressures corresponding to various values of pressure applied to a blood pressure cuff, a system for detecting spurious low values in said table, comprising:

means for comparing each of said values to the smaller of any adjacent values in said table; and designating said value as spurious if said value is smaller than a predetermined percentage of said smaller adjacent value.

2. The system of claim 1 wherein said predetermined percentage is 75%.

3. The system of claim 1 wherein said value is designated as being spurious only if said smaller adjacent value is larger than a predetermined threshold level.

4. The system of claim 3 wherein said predetermined threshold level is approximately equal to one-half the average of all non-zero values in said table.

5. In an apparatus for the measurement of blood pressure in which a table of values is generated indicative of the blood pressure corresponding to various values of pressure applied to a blood pressure cuff, a system for detecting spurious high values in said table, comprising:

means for determining the two largest values in said table;

means for determining the difference between the cuff pressures corresponding to said two largest values with the larger of any adjacent value;

means for comparing the largest of said two largest values with the larger of any values adjacent to said largest value; and means for detecting as a spurious high value if the cuff pressures corresponding to said two largest values are different from each other by more than a predetermined magnitude and the larger of the values adjacent to said largest value is less than a predetermined percentage of said largest value.

6. The system of claim 5 wherein said two largest values in said table must not correspond to adjacent blood pressure measurements in order to designate said largest value as a spurious high value.

7. The system of claim 5 wherein said predetermined percentage is 50%.

8. An apparatus for the measurement of blood pressure, comprising:

a pressure cuff attachable to a patient adjacent a blood vessel;

means for changing pressure in the cuff to apply pressure to the patient;

means communicating with the cuff for measuring a quantity representative of the patient's blood pressure;

means for forming a table of values attained by said quantity as the applied pressure is changed, said values generally increasing from low values at applied pressures at one end of the table greater than systolic to a maximum value at applied pressures between systolic and diastolic, said values generally increasing from low values at applied pressures at an opposite end of said table less than diastolic to said maximum value;

means for selecting each value in said table as a candidate value and for determining which is the smaller of the values in said table adjacent said candidate value;

means for establishing a threshold level;

means for comparing said smaller value with said threshold value and for comparing said candidate value with said smaller value;

means for selecting said candidate value for correction if said smaller value is greater than said threshold value and said candidate value is less than a predetermined percentage of said smaller value;

means for averaging a predetermined number of values adjacent either side of each of said selected candidated values in said table; and means for changing said selected candidate value to said average.

9. The apparatus of claim 8 wherein said predetermined percentage is 75%.

10. The apparatus of claim 8 wherein said predetermined threshold level is substantially about one half the average of all the non-zero values in the table.

11. The apparatus of claim 8 wherein said predetermined number of values comprises two except for selected values which are next to the last values in the table, in which case said predetermined number is 1.

12. An apparatus for the measurement of blood pressure, comprising:

a pressure cuff attachable to a patient adjacent a blood vessel;

means for changing pressure in the cuff to apply pressure to the patient;

means communicating with the cuff for measuring a quantity representative of the patient's blood pressure;

means for forming a table of values attained by said quantity as the applied pressure is changed, said values generally increasing from low values at applied pressures at one end of the table greater than systolic to a maximum value at applied pressures between systolic and diastolic, said values generally increasing from low values at applied pressures at an opposite end of said table less than diastolic to said maximum value;

means for determining the two largest values in the table; means for determining the separation of the two largest values within the table;

means for comparing the largest value in the table with the larger adjacent value;

means for selecting said largest value as a spurious large value if the two largest values are separated apart from each other by at least a predetermined difference in said applied pressure and the larger value adjacent to said largest value is less than a predetermined percentage of said largest value;

means for averaging a predetermined number of values adjacent either side of each of said selected values; and means for changing said selected values to said average.

13. The apparatus of claim 12 wherein said predetermined separation comprises being adjacent.

14. The apparatus of claim 12 wherein said predetermined percentage is 50%.

15. A method for the measurement of blood pressure, comprising the steps of:

attaching a pressure cuff to a patient adjacent a blood vessel;

changing the pressure in the cuff to apply pressure to the patient;

providing communication with the cuff for measuring a quantity representative of the patient's blood pressure;

forming a table of values attained by said quantity as the applied pressure is changed, said values generally increasing from low values at applied pressures at one end of the table greater than systolic to a maximum value at applied pressures between systolic and diastolic, said values generally increasing from low values at applied pressures at an opposite end of said table less than diastolic to said maximum value;

selecting each value in said table as a candidate value and determining which is the smaller of the values in said table adjacent each candidate value;

establishing a threshold level;

comparing said smaller value with said threshold value and said candidate value with said smaller value;

selecting said candidate value for correction if said smaller value is greater than said threshold value and said candidate value is less than a predetermined percentage of said smaller value;

averaging a predetermined number of values adjacent either side of each of said selected candidate values in said table; and changing said selected value to said average.

16. The method of claim 15 wherein said predetermined percentage is 75%.

17. The method of claim 15 wherein said predetermined threshold level is substantially about one half the average of all the non-zero values in the table.

18. The method of claim 15 wherein said predetermined member comprises two except for selected values which are next to the last values in the table in which case said predetermined number is 1.

19. A method for the measurement of blood pressure, comprising the steps of:

attaching a pressure cuff to a patient adjacent a blood vessel;

changing the pressure in the cuff to apply pressure to the patient;

providing communication with the cuff for measuring a quantity representative of the patient's blood pressure;

forming a table of values attained by said quantity as the applied pressure is changed, siad values generally increasing from low values at applied pressures at one end of the table greater than systolic to a maximum value at applied pressures between systolic and diastolic, said values generally increasing from low values at applied pressures at an opposite end of said table less than diastolic to said maximum value;

determining the two largest values in the table;

determining the separation of the two largest values within the table;

comparing the largest value in the table with the larger adjacent value;

selecting said largest value as a spurious large value if the two largest values are separated apart from each other by at least a predetermined difference in applied pressure within a predetermined separation and the larger value adjacent to said largest value is less than a predetermined percentage of said largest value;

averaging a predetermined number of values adjacent either side of each of said selected values;

averaging a predetermined number of values adjacent either side of each of said selected values; and changing said selected values to said average.

20. The method of claim 19 wherein said predetermined separation comprises being adjacent.

21. The method of claim 19 wherein said predetermined percentage is 50%.

* * * * *